US010881328B2

United States Patent
Fu et al.

(10) Patent No.: US 10,881,328 B2
(45) Date of Patent: Jan. 5, 2021

(54) SYSTEMS AND METHODS FOR DETERMINING AND TRACKING SUBJECT POSITIONING

(71) Applicant: Allen Medical Systems, Inc., Batesville, IN (US)

(72) Inventors: Yongji Fu, Harrison, OH (US); Benjamin E. Howell, Fuquay-Varina, NC (US); Jeffrey C. Marrion, Acton, MA (US); Todd P. O'Neal, Fairfield, OH (US); Joshua A. Williams, West Harrison, IN (US)

(73) Assignee: Allen Medical Systems, Inc., Batesville, IN (US)

( * ) Notice: Subject to any disclaimer, the term of this patent is extended or adjusted under 35 U.S.C. 154(b) by 436 days.

(21) Appl. No.: 15/336,082

(22) Filed: Oct. 27, 2016

(65) Prior Publication Data

US 2017/0119285 A1 May 4, 2017

Related U.S. Application Data

(60) Provisional application No. 62/248,387, filed on Oct. 30, 2015.

(51) Int. Cl.
*A61B 5/11* (2006.01)
*A61B 5/00* (2006.01)
(Continued)

(52) U.S. Cl.
CPC .......... *A61B 5/1127* (2013.01); *A61B 5/0075* (2013.01); *A61B 5/015* (2013.01);
(Continued)

(58) Field of Classification Search
CPC ..... A61B 5/1127; A61B 5/0075; A61B 5/015; A61B 5/742; A61B 2090/3979
See application file for complete search history.

(56) References Cited

U.S. PATENT DOCUMENTS

| 4,769,584 A | 9/1988 | Irigoyen et al. |
| 5,249,581 A * | 10/1993 | Horbal ................. A61B 5/1077 600/407 |

(Continued)

OTHER PUBLICATIONS

Adams Industries Inc. Thermal Tape and Markers <https://www.adamsindustries.com/Thermal-Tape-and-Markers.html> (Year: 2014).*

*Primary Examiner* — Patrick Fernandes
(74) *Attorney, Agent, or Firm* — Dinsmore & Shohl LLP

(57) ABSTRACT

Systems and methods for determining and tracking a positioning of a subject and displaying an image of a model of a subject are disclosed. A system includes a plurality of thermal markers, one or more thermal imaging devices arranged to capture baseline and updated infrared images of the surface and the thermal markers, and a computing device communicatively coupled to the thermal imaging devices. A first thermal marker is arranged at a first location relative to the surface. The computing device receives the baseline and updated infrared images and determines a corrective movement for at least one of the subject and the surface to align the thermal markers in the updated infrared image with the thermal markers in the baseline infrared image based on a location of the thermal markers in the baseline infrared image and a location of the thermal markers in the updated infrared image.

20 Claims, 9 Drawing Sheets

(51) Int. Cl.
 *A61B 5/01* (2006.01)
 *A61B 90/00* (2016.01)

(52) U.S. Cl.
 CPC .............. *A61B 5/742* (2013.01); *A61B 90/39* (2016.02); *A61B 2090/3979* (2016.02); *A61B 2505/05* (2013.01); *A61B 2576/00* (2013.01)

(56) References Cited

U.S. PATENT DOCUMENTS

| | | |
|---|---|---|
| 5,588,705 A | 12/1996 | Chang |
| 5,794,286 A | 8/1998 | Scott et al. |
| 6,390,982 B1 * | 5/2002 | Bova .................... A61B 6/5247 128/916 |
| 6,505,365 B1 | 1/2003 | Hanson et al. |
| 7,600,281 B2 | 10/2009 | Skripps |
| 8,020,227 B2 | 9/2011 | Dimmer et al. |
| 8,676,293 B2 | 3/2014 | Breen et al. |
| 8,777,878 B2 | 7/2014 | Deitz |
| 8,782,832 B2 | 7/2014 | Blyakher et al. |
| 2010/0045954 A1 * | 2/2010 | Onvlee ............... G03F 7/70116 355/67 |
| 2011/0015521 A1 * | 1/2011 | Faul .................... A61N 5/1049 600/426 |
| 2015/0057485 A1 * | 2/2015 | Carey ................. A61N 5/1049 600/1 |

* cited by examiner

SYSTEMS AND METHODS FOR DETERMINING AND TRACKING SUBJECT POSITIONING

CROSS-REFERENCE TO RELATED APPLICATION

The present application claims priority to U.S. Provisional Patent Application Ser. No. 62/248,387, filed Oct. 30, 2015 and entitled "Systems and Methods for Determining and Tracking Subject Positioning," the entire contents of which is incorporated herein by reference.

BACKGROUND

Field

The present specification generally relates to tracking systems and methods and, more specifically, to tracking systems and methods that incorporate thermal imaging.

Technical Background

It may be necessary to determine and/or track a subject's positioning during a surgical procedure. For example, a surgical procedure may require that a subject be initially oriented in a first position, subsequently repositioned to a second position, and then repositioned a second time back to the first position. Existing methods require medical staff to estimate the positioning of the subject for each of the positions, which may be time consuming and inaccurate.

Accordingly, a need exists for systems and methods that provide medical staff with an ability to accurately determine and/or track the positioning of a subject.

SUMMARY

In one embodiment, a system for determining a positioning of a subject includes a plurality of thermal markers, one or more thermal imaging devices arranged to capture a baseline infrared image and an updated infrared image of the surface and the plurality of thermal markers, and a computing device communicatively coupled to the one or more thermal imaging devices. A first thermal marker of the plurality of thermal markers is arranged at a first location relative to the surface. The computing device receives the baseline infrared image and the updated infrared image and determines a corrective movement for at least one of the subject and the surface to align the thermal markers in the updated infrared image with the thermal markers in the baseline infrared image based on a location of the plurality of thermal markers in the baseline infrared image and a location of the plurality of thermal markers in the updated infrared image.

In another embodiment, a method of positioning a subject on a surface includes placing a plurality of thermal markers on a body of the subject, capturing baseline infrared images of the subject and the plurality of thermal markers with one or more thermal imaging devices, and transmitting the baseline infrared images and the updated infrared images to a computing device. The computing device determines a corrective movement to align the thermal markers in the updated image with the thermal markers in the baseline image based on a location of the plurality of thermal markers in the baseline infrared image and a location of the plurality of thermal markers in the updated infrared image. The method further includes applying the corrective movement to at least one of the subject and the surface to position the subject on the surface.

In yet another embodiment, a system for positioning a subject on a surface includes a plurality of thermal markers, one or more thermal imaging devices arranged to capture a baseline infrared image and an updated infrared image of the surface and the plurality of thermal markers, and a computing device communicatively coupled to the one or more thermal imaging devices. A first thermal marker of the plurality of thermal markers is arranged at or near a joint of the subject positioned on the surface and each of the plurality of thermal markers emits thermal energy that is distinguishable from thermal energy emitted by the subject positioned on the surface, the surface, and one or more objects proximate the surface. The computing device receives the baseline infrared image and the updated infrared image and determines a corrective movement for at least one of the subject and the surface to align the plurality of thermal markers in the updated infrared image with the plurality of thermal markers in the baseline infrared image based on a location of the plurality of thermal markers in the baseline infrared image and a location of the plurality of thermal markers in the updated infrared image.

In yet another embodiment, a system for displaying a model of a subject includes one or more thermal imaging devices and a computing device communicatively coupled to the one or more thermal imaging devices. The computing device includes a processing device and a non-transitory, processor-readable storage medium having one or more processor readable and executable instructions that, when executed, cause the processing device to receive one or more infrared images from the one or more thermal imaging devices. The infrared images contain a plurality of thermal markers positioned relative to a surface, and at least one of the plurality of thermal markers is positioned on a subject located on the surface. The non-transitory, processor-readable storage medium further has one or more processor readable and executable instructions that, when executed, cause the processing device to determine a location of the plurality of thermal markers with respect to the subject from the one or more infrared images. The plurality of thermal markers produce thermal energy that is identifiable and distinguishable from thermal energy emitted by the surface and the subject. The non-transitory, processor-readable storage medium further has one or more processor readable and executable instructions that, when executed, cause the processing device to map the location of the one or more thermal markers to a model that represents the subject and the positioning of the subject and display the model with a plurality of indicators thereon. Each of the plurality of indicators corresponds to each of the plurality of thermal markers.

In yet another embodiment, a method for tracking a positioning of a subject includes receiving, by a processing device, one or more infrared images of the subject and determining, by the processing device, a location of a plurality of thermal markers with respect to the subject from the one or more infrared images. The plurality of thermal markers produce thermal energy that is identifiable and distinguishable from thermal energy produced by the subject, and at least one thermal marker is located at a first location on a body of the subject. The method further includes mapping, by the processing device, the location of the one or more thermal markers to a model that represents the subject and the positioning of the subject and displaying, by the processing device, the model with a plurality of indicators thereon. The plurality of indicators corresponds to the plurality of thermal markers.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1A:
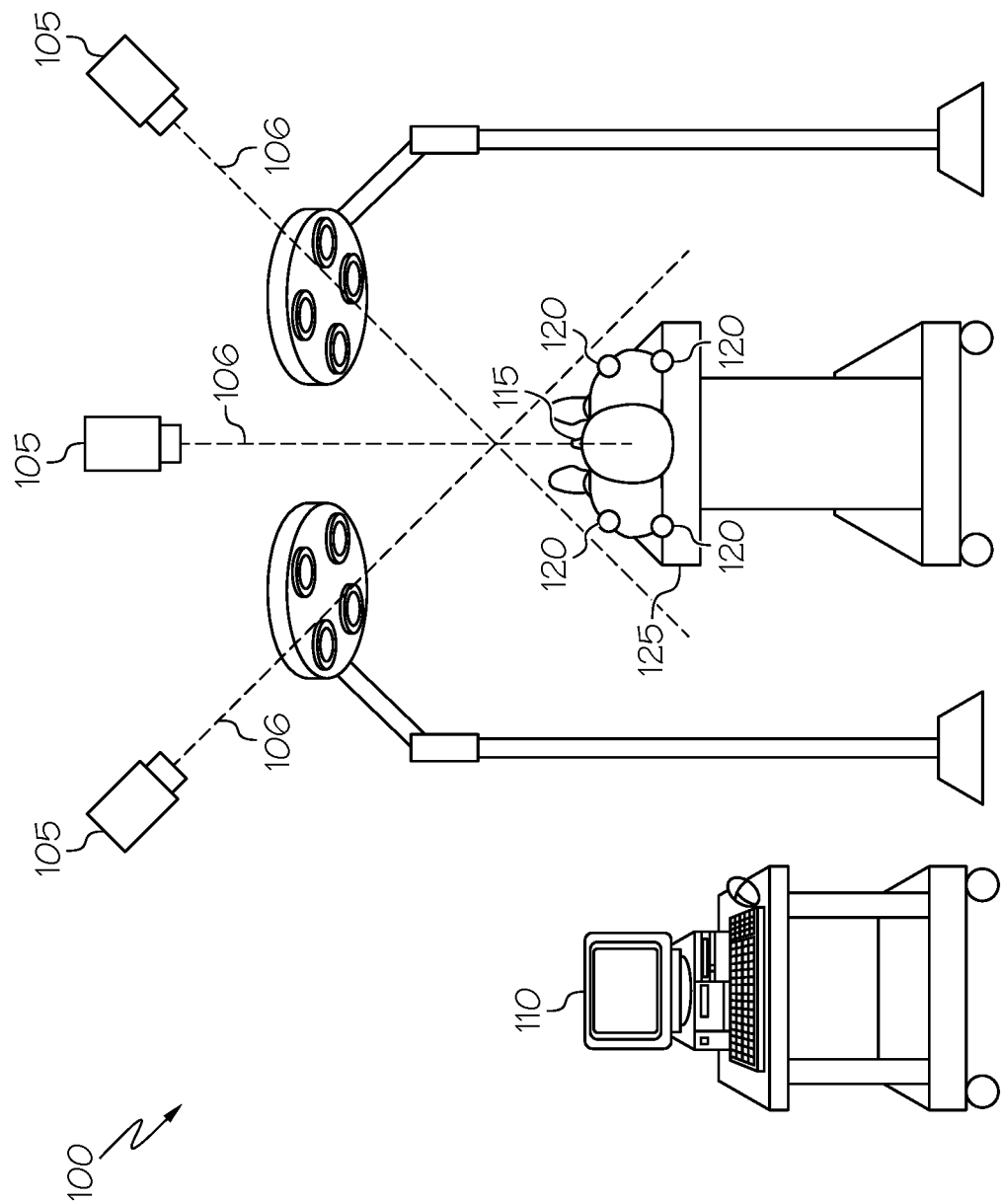
FIG. 1A schematically depicts an illustrative subject tracking system according to one or more embodiments shown or described herein.

Reference will now be made in detail to embodiments of systems and methods for tracking the positioning of a subject during surgery, examples of which are illustrated in the accompanying drawings. Whenever possible, the same reference numerals will be used throughout the drawings to refer to the same or like parts. One embodiment of a system for tracking the positioning of a subject is depicted in FIG. 1A, in which the system includes one or more thermal imaging devices, a computing device, and a plurality of thermal markers, where at least one of the thermal markers is arranged at a first location on the body of the subject. The one or more thermal imaging devices obtain one or more thermal images of the subject, the thermal markers, and/or the surface upon which the subject is positioned. The computing device receives the one or more thermal images, analyzes the images to determine the location of the thermal markers, maps the thermal markers to a model, and displays the model with indicators thereon corresponding to the location of the thermal markers. As the positioning of the subject is changed, the computing device detects an updated location of the thermal markers from the images that are received from the thermal imaging devices, maps the updated positioning on the model, and displays the model with the updated positioning. Optionally, the computing device may further provide instructions for returning the positioning of the subject to an original positioning or moving the subject to a new positioning. Accordingly, the positioning of a subject can be accurately tracked such that, if the subject is moved, the subject can be moved again to return to the previous positioning. In addition, the system can be coupled to automated surgical surfaces to automatically move the subject, thereby avoiding the need to breach a sterile field surrounding the subject during a procedure.

The phrase "communicatively coupled" is used herein to describe the interconnectivity of various components of the system for tracking the positioning of a subject and means that the components are connected either through wires, optical fibers, or wirelessly such that electrical, optical, and/or electromagnetic signals may be exchanged between the components. It should be understood that other means of connecting the various components of the system not specifically described herein are included without departing from the scope of the present disclosure.

As used herein, the term "positioning" generally refers to how a subject is oriented on a surface, including the location and orientation of various body parts relative to other body parts and/or the surface. For example, a subject's positioning may be that the subject is face down with the head tilted to the right, the arms raised above the shoulders, the legs parallel to each other, and the back flattened. The subject's positioning may change, for example, if the subject's back is arched, the head is moved, the legs are moved, and/or the like. In addition, "positioning" may also refer to a location of thermal markers relative to the subject's body and/or a configuration of the surface on which a subject is posed.

Referring to FIG. 1A, a system 100 for determining a positioning of a subject is depicted. The system 100 includes at least one thermal imaging device 105 (three depicted in FIG. 1A) communicatively coupled to a computing device 110. In addition, the system 100 includes a plurality of thermal markers 120, each of which is arranged on or around the body of a subject 115, on or around a surface 125 supporting the subject 115, and/or on one or more other objects adjacent to the body of the subject 115 and/or the surface 125. The system 100 is generally arranged and configured such that each thermal imaging device 105 is positioned to image the subject 115, the thermal markers 120, and/or the surface 125 and transmit images to the computing device 110.

Various components of the system 100 may generally be located in a room or an area that is used for subject care. For example, in some embodiments, certain components of the system 100 may be located in an operating room, a surgical suite, a recovery room, a subject's room, or the like. In some embodiments, all of the components of the system 100 may be located in the same room or area. In other embodiments, certain components of the system 100 may be remotely located. In a nonlimiting example, the computing device 110 and/or one or more components thereof may be remotely located. For example, the computing device 110 may be a remotely located server that is communicatively coupled to each thermal imaging device 105 and a display that are located in the same room or area.

Figure 2:
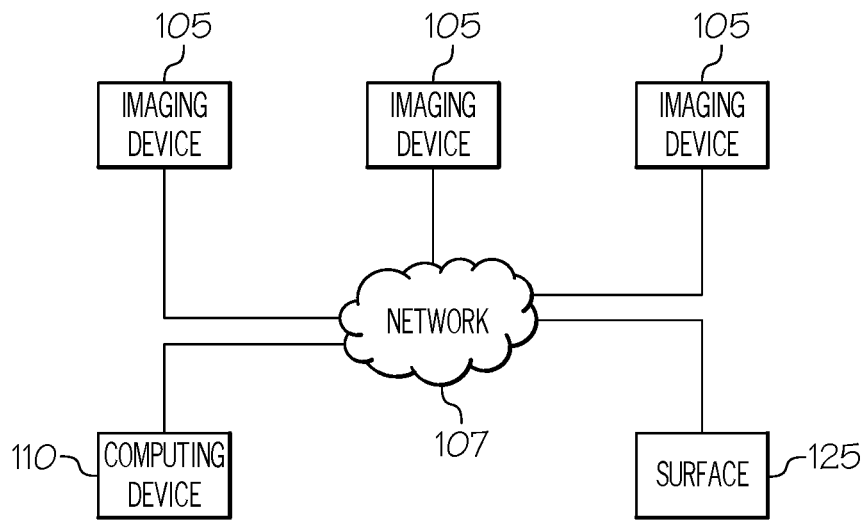
FIG. 2 schematically depicts a block diagram of the interconnectivity of the various components of the subject tracking system of FIG. 1A according to one or more embodiments shown or described herein.

Certain components of the system 100 are communicatively coupled to each other to transmit data. For example, as depicted in FIG. 2, each thermal imaging device 105, the computing device 110, and the surface 125 may be connected via a network 107. The network 107 may include a wide area network (WAN), such as the Internet, a local area network (LAN), a mobile communications network, a public service telephone network (PSTN), a personal area network (PAN), a metropolitan area network (MAN), a virtual private network (VPN), or any other suitable network.

Referring again to FIG. 1A, each thermal imaging device 105 is generally positioned such that the thermal imaging device 105 is aimed at the subject 115, the thermal markers 120, the surface 125, and/or one or more other objects adjacent to the body of the subject 115 and/or the surface 125. That is, an optical axis 106 of each thermal imaging device 105 extends towards at least a portion of the subject 115, the thermal markers 120, the surface 125, and/or the other objects. In the embodiments described herein, the optical axis 106 refers to an imaginary line defining the path along which electromagnetic radiation (such as thermal radiation) propagates to and through the thermal imaging device 105. In embodiments, each thermal imaging device 105 may be mounted on a wall, on a ceiling, or in a corner. In some embodiments, each thermal imaging device 105 may be coupled to various apparatuses, such as floor stands, surgical lamps, IV poles, induction hoods, or the like.

While FIG. 1A depicts three thermal imaging devices 105, it should be understood that any number of thermal imaging devices 105 may be used in conjunction with the system 100. For example, in some embodiments, the system 100 may include a single thermal imaging device. In other embodiments, the system 100 may include two or more thermal imaging devices 105. In some embodiments, the number of thermal imaging devices 105 in the system may be sufficient to render a three dimensional (3D) image or heat map of the subject 115, the surface 125, and/or the one or more other objects.

In embodiments where the system 100 includes a plurality of thermal imaging devices 105, such thermal imaging devices 105 may be spaced apart or may be arranged next to each other. For example, each of the thermal imaging devices 105 may be spaced at a distance from each other such that the respective optical axis 106 of each thermal imaging device 105 is at a different angle with respect to the surface 125. For example, in embodiments, the thermal imaging devices 105 may be oriented relative to one another and the surface 125 such that the optical axes 106 of respective thermal imaging devices 105 are non-parallel with one another, as depicted in FIG. 1A. As such, each thermal imaging device 105 captures a different angle of the subject 115, the thermal markers 120, the surface 125, and/or other objects. The distance between the thermal imaging devices 105 is not limited by this disclosure, and may generally be any distance. In another example, the thermal imaging devices 105 may be arranged next to each other and each thermal imaging device 105 is configured to obtain an image that partially overlaps an image obtained by at least one adjacent thermal imaging device 105 such that the images can be stitched together to obtain a panoramic image.

The computing device 110 is communicatively coupled to each thermal imaging device 105 such that the computing device 110 receives data transmissions, particularly data transmissions containing image data, from each thermal imaging device 105. Certain wired or wireless connections now known or later developed for transmitting such data should generally be understood as being included within the scope of the present disclosure.

The computing device 110 and/or one or more components thereof are arranged such that the thermal images are received from each thermal imaging device 105 and information and images are displayed to various personnel that are caring for the subject 115. Thus, at least one component of the computing device 110 (such as a display) may be arranged such that the personnel can view the displayed images. Accordingly, the computing device 110 and/or one or more components thereof may be located in the same room or area of the subject 115 and each thermal imaging device 105 or an adjacent room or area. The computing device 110 and/or one or more components thereof may be freestanding, mounted to a wall, coupled to other equipment, arranged on a cart, and/or the like.

The plurality of thermal markers 120 may generally be arranged on or around the subject 115, on or around the surface 125, and/or on one or more other objects (e.g., accessories, tops, head positioners, torso supports, and/or the like) adjacent to the body of the subject 115 and/or the surface 125 such that thermal radiation emitted by the thermal markers 120 is within the field of view of at least one thermal imaging device 105. Thus, in some embodiments, the subject 115 may be positioned on the surface 125 in the room or area with each thermal imaging device 105 arranged around the subject 115, the surface 125, and/or other objects.

Each thermal imaging device 105 may be any imaging device that is suitable for obtaining images within the infrared (IR) spectrum. As used herein, the term "images" or "image" refers video images (i.e., a sequence of consecutive images) and/or still images (including still images isolated from video images) captured in at least the infrared spectrum. That is, each thermal imaging device 105 may be a device that obtains images via IR thermography to capture radiation in the long-infrared range of the electromagnetic spectrum. The long-infrared range of the electromagnetic spectrum may be electromagnetic radiation having a wavelength from about 9 micrometers (µm) to about 14 µm, including about 9 µm, about 10 µm, about 11 µm, about 12 µm, about 13 µm, about 14 µm or any value or range between any two of these values (including endpoints). A nonlimiting example of a thermal imaging device includes any one of the infrared cameras sold by FLIR Systems, Inc. (Wilsonville, Oreg.).

Since IR radiation is emitted by all objects having a temperature above absolute zero, a thermal imaging device 105 that obtains images via IR thermography allows for imaging an environment with or without visible illumination. The thermal imaging device 105 obtains images based on temperature and the resulting images indicate variations in temperature. Thus, in the images produced by the thermal imaging device 105, objects are distinguishable from one another and the background based on variations in temperature. For example, humans become distinguishable in a typical room temperature environment because their body temperatures are greater than objects that are at or below room temperature and because the human body emits IR radiation at a different temperature than such objects at, below, or above room temperature.

Moreover, the thermal imaging device 105 can image certain target objects (such as the subject 115, the surface 125, other objects, and/or the thermal markers 120) even if the field of view between the thermal imaging device 105 and the target object is obstructed or partially obstructed by items that are at a lower temperature and allow thermal energy to penetrate therethrough. This is because the target object radiates thermal energy that extends around and/or through the obstruction. For example, if the field of view for a thermal imaging device 105 is partially blocked by an obstruction such as a sheet, a surgical drape, a hospital gown, clothing, and/or the like, the thermal imaging device 105 may nevertheless detect the IR radiation emitted by the target object if the target object emits sufficient thermal energy to pass around and/or through the obstruction.

In various embodiments, the thermal imaging device 105 may incorporate or be coupled to various other components to provide additional functionality. For example, in some embodiments, the thermal imaging device 105 may incorporate an imaging device that obtains images within the visible spectrum of electromagnetic radiation (e.g., radiation having a wavelength from about 390 nanometers (nm) to about 700 nm) in addition to capturing images in the infrared spectrum. In another example, the thermal imaging device 105 may incorporate various mechanisms that allow the thermal imaging device 105 to move, such as to change location, pan, tilt, scan, and/or the like.

In the embodiments described herein, the computing device 110 is a computer that receives thermal images in the form of image data, processes the image data, and provides information. In some embodiments, the computing device 110 may be particularly configured to process thermal image data and determine subject positioning by using specific components not commonly included in a general purpose computer. For example, in some embodiments, various components of the computing device 110 may be integrated with at least one thermal imaging device 105. That is, the thermal imaging device 105 and at least one component of the computing device 110 may be particularly integrated to obtain and process thermal images for the purpose of determining a positioning of the subject 115.

Figure 3:
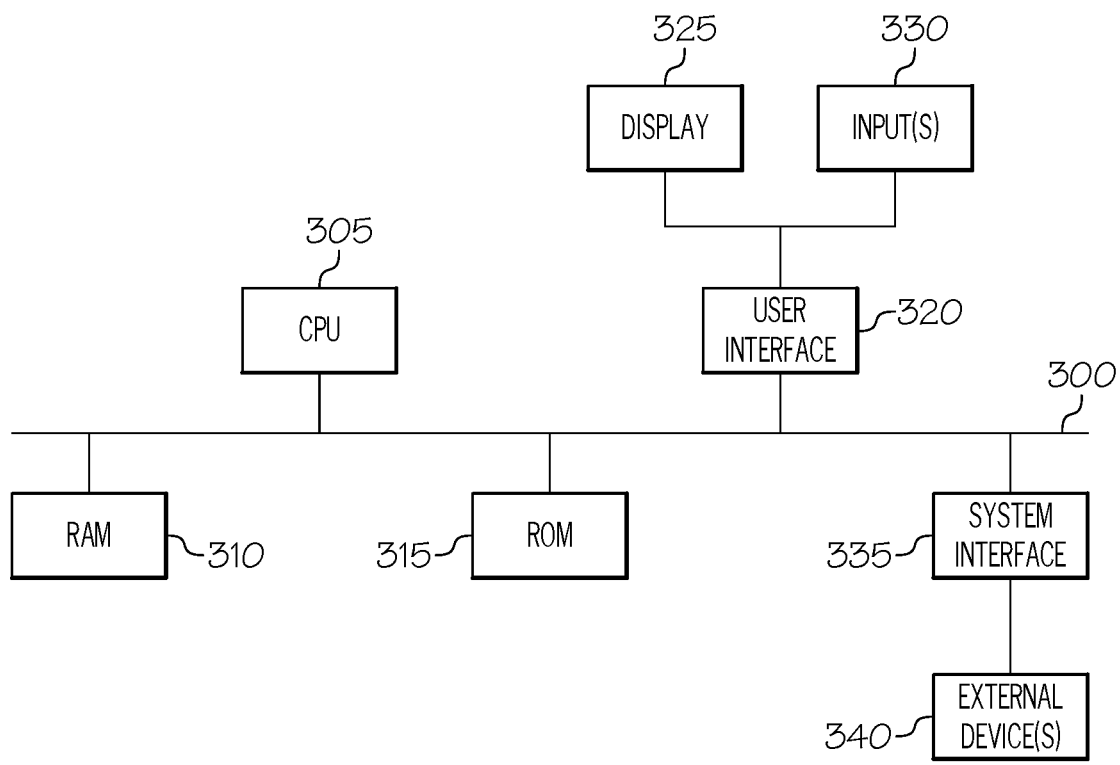
FIG. 3 schematically depicts a block diagram of illustrative computing device components according to one or more embodiments shown or described herein.

To receive the image data, process the thermal images, and provide information, the computing device 110 includes a plurality of hardware components. Referring also to FIG. 3, various illustrative hardware components of the computing device 110 are depicted. A bus 300 may interconnect the various components. A processing device, such as a computer processing unit (CPU) 305, may be the central processing unit of the computing device 110, performing calculations and logic operations required to execute a program. The CPU 305, alone or in conjunction with one or more of the other elements disclosed in FIG. 3, is an illustrative processing device, computing device, processor, or combination thereof, as such terms are used within this disclosure. Memory, such as read only memory (ROM) 315 and random access memory (RAM) 310, may constitute illustrative memory devices (i.e., non-transitory, processor-readable storage media). Such memory 310, 315 may include one or more program instructions thereon that, when executed by the CPU 305, cause the CPU 305 to complete various processes, such as the processes described herein. Optionally, the program instructions may be stored on a tangible computer-readable medium such as a digital disk, flash memory, a memory card, a USB drive, an optical disc storage medium, such as a Blu-ray™ disc, a digital versatile disc (DVD) a compact disc (CD), and/or other non-transitory processor-readable storage media.

An optional user interface 320 may permit information from the bus 300 to be displayed on a display 325 in audible, visual, graphic, or alphanumeric format. The user interface 320 may also include one or more inputs 330 that allow for transmission to and receipt of data from input devices such as a keyboard, a mouse, a joystick, a touch screen, a remote control, a pointing device, a video input device, an audio input device, a haptic feedback device, and/or the like. In some embodiments, the display 325 and the inputs 330 may be combined into a single device, such as a touchscreen display or the like. Such a user interface 320 may be used, for example, to allow a user to view thermal images of the subject 115 (and the thermal markers 120 thereon), determine which other objects are being utilized (e.g., accessories such as tops, head positioners, torso supports, and/or the like), view information regarding positioning of the subject 115, receive instructions for manually adjusting the positioning of the subject 115, provide inputs for automatically adjusting the positioning of the subject 115, view a body temperature of the subject 115, and/or the like.

A system interface 335 may generally provide the computing device 110 with an ability to interface with one or more external devices 340, particularly the one or more other portions of the system 100, such as, for example, the thermal imaging devices 105 or the surface 125. Communication with external devices 340 may occur using various communication ports (not shown). An illustrative communication port may be attached to a communications network, such as the network 107 (FIG. 2) described in greater detail herein.

Referring again to FIG. 1A, each of the thermal markers 120 is generally any device or object that can be arranged relative to the surface 125, such as on the subject 115 positioned on the surface 125, directly on the surface 125, and/or other objects such as accessories or the like coupled to the surface 125. In addition, each of the thermal markers 120 is generally any device or object that emits thermal energy to provide a distinct and distinguishable reference point when imaged by the thermal imaging device 105. Thus, the type of thermal marker 120 are not limited by the present disclosure. In some embodiments, each thermal marker 120 may be any commercially available thermal marking product now known or later developed. One non-limiting example of a thermal marking product includes products sold by Adams Industries, Inc. (Los Angeles, Calif.).

The thermal markers 120 are generally attachable and positionable relative to the surface 125. For example, the thermal markers 120 may be attachable and positionable on the subject 115 such as with adhesive material or the like. That is, in some embodiments, the thermal markers 120 may be shaped and sized such that they cover a particular portion of the subject's body, such as, for example, a joint. Because certain joints may be relatively close together than other joints, the thermal markers 120 may be shaped and sized such that they can be distinguished from each other when placed over adjacent joints that are close together, yet also not so small that they are not detectable by the thermal imaging device 105. Accordingly, it should be understood that the thermal markers 120 may be shaped and sized to allow for differentiation of adjacent body parts, yet large enough to be imaged by the thermal imaging device 105.

In addition, the thermal markers 120 may also be attachable and positionable relative to the surface 125, such as when the thermal markers 120 are directly attached to the surface 125, such as with adhesive material or the like. That is, the thermal markers 120 may be shaped and sized such that they cover a particular portion of the surface 125, such as various surface features. For example, the thermal markers 120 may be arranged on joints, connection points, discrete portions of the surface and/or the like such that the surface features provide a reference point that can be used to determine positioning of the subject 115 vis-à-vis the surface 125. The thermal markers 120 may be arrangeable on the surface 125 such that a positioning and an orientation of the surface 125 can be determined. Accordingly, it should be understood that the thermal markers 120 are attachable and positionable relative to the surface, either directly to the surface 125 or to a subject positioned on the surface 125.

In addition, the thermal markers 120 may also be attachable and positionable relative to one or more other objects, such as accessories or the like, which may be coupled to the surface 125, supporting the subject 115, adjacent to the surface 125 and/or the subject, and/or the like. The thermal markers 120 may be attachable and positionable with adhesive material or the like. That is, the thermal markers 120 may be shaped and sized such that they cover a particular portion of the other object, such as various surface features. For example, the thermal markers 120 may be arranged on joints, connection points, discrete portions of the other object and/or the like such that the surface features provide a reference point that can be used to determine the type of other object, and/or the location and positioning of the other object relative to the subject 115 and/or the surface 120. In turn, may also be used to determine positioning of the subject 115 vis-à-vis the other objects (e.g., such as when the other object is a head positioner or other accessory that interacts with the subject 115). The thermal markers 120 may be arrangeable on the other object such that a positioning and an orientation of the other object can be determined.

The thermal markers 120 emit thermal energy that, when imaged by a thermal imaging device 105, is identifiable and distinguishable from the subject 115 and the surface 125 by the computing device 110 when the image data is processed. That is, the thermal markers 120 radiate thermal energy that is at a temperature that differs from the thermal energy radiated by the subject 115 and/or the surface 125. Accordingly, the thermal markers 120 may radiate thermal energy at a temperature that is colder than the thermal energy radiated by the subject 115 or hotter than the thermal energy radiated by the subject 115 such that the thermal markers 120 are distinguishable from the subject 115 in the image captured by the thermal imaging device 105. In addition, the thermal markers 120 may radiate thermal energy at a temperature that is colder than the thermal energy radiated by the surface 125 or hotter than the thermal energy radiated by the surface 125 such that the thermal markers 120 are distinguishable from the surface 125 in the image captured by the thermal imaging device 105.

The difference between the temperature of the thermal energy radiated by the thermal markers 120 and the thermal energy radiated by the subject 115 and/or the surface 125 is not limited by the present disclosure, and may generally be any temperature difference that is distinguishable by the computing device 110 when the image data is processed. For example, the difference may be from about 1° C. to about 50° C., including about 1° C., about 5° C., about 10° C., about 20° C., about 30° C., about 40° C., about 50° C., or any value or range between these two values (including endpoints). It should be understood that other temperature differences between the thermal energy radiated by the thermal markers 120 and the thermal energy radiated by the subject 115 and/or the surface 125 are contemplated and possible. In some embodiments, the temperature of the thermal energy radiated by the thermal markers 120 may be such that it does not injure the subject 115, such as by causing tissue damage or the like. For example, if the thermal energy radiated by the thermal markers 120 is too hot, it may burn the subject 115. In some embodiments, the thermal markers 120 may include a shielded surface or the like that is positioned between the subject 115 and a thermal energy emitting portion of the thermal marker 120 to shield the subject 115 from the thermal energy emitted by the thermal marker.

In some embodiments, the temperature of the thermal energy emitted by the thermal markers 120 may be substantially the same for each of the thermal markers 120. In other embodiments, the temperature of the thermal energy emitted by the thermal markers 120 may vary across all of the thermal markers. In these embodiments, the difference in thermal energy emitted by the various markers may assist in differentiating the portions of the subject 115 and/or the surface 125 to which the thermal markers 120 are attached in a captured image. That is, each portion of the subject 115 and the surface 125 may be marked with a thermal marker 120 that emits a different wavelength of thermal energy. In still other embodiments, the temperature of the thermal energy emitted by the thermal markers 120 attached to the subject 115 may be different than the temperature of the thermal energy emitted by the thermal markers 120 attached to the surface 125. In these embodiments, the difference in thermal energy emitted by the various markers may assist in differentiating the subject 115 and the surface 125 to which the thermal markers 120 are attached in a captured image. When the temperature of the thermal energy emitted by the thermal markers 120 varies, a user may place thermal markers emitting a first temperature in a first location on the subject 115 and/or the surface 125 and place thermal markers emitting a second temperature in a second location on the subject 115 and/or the surface 125 such that the first location and the second location can be distinguished from one another, which may further help determine the positioning of the subject 115.

Figure 1B:
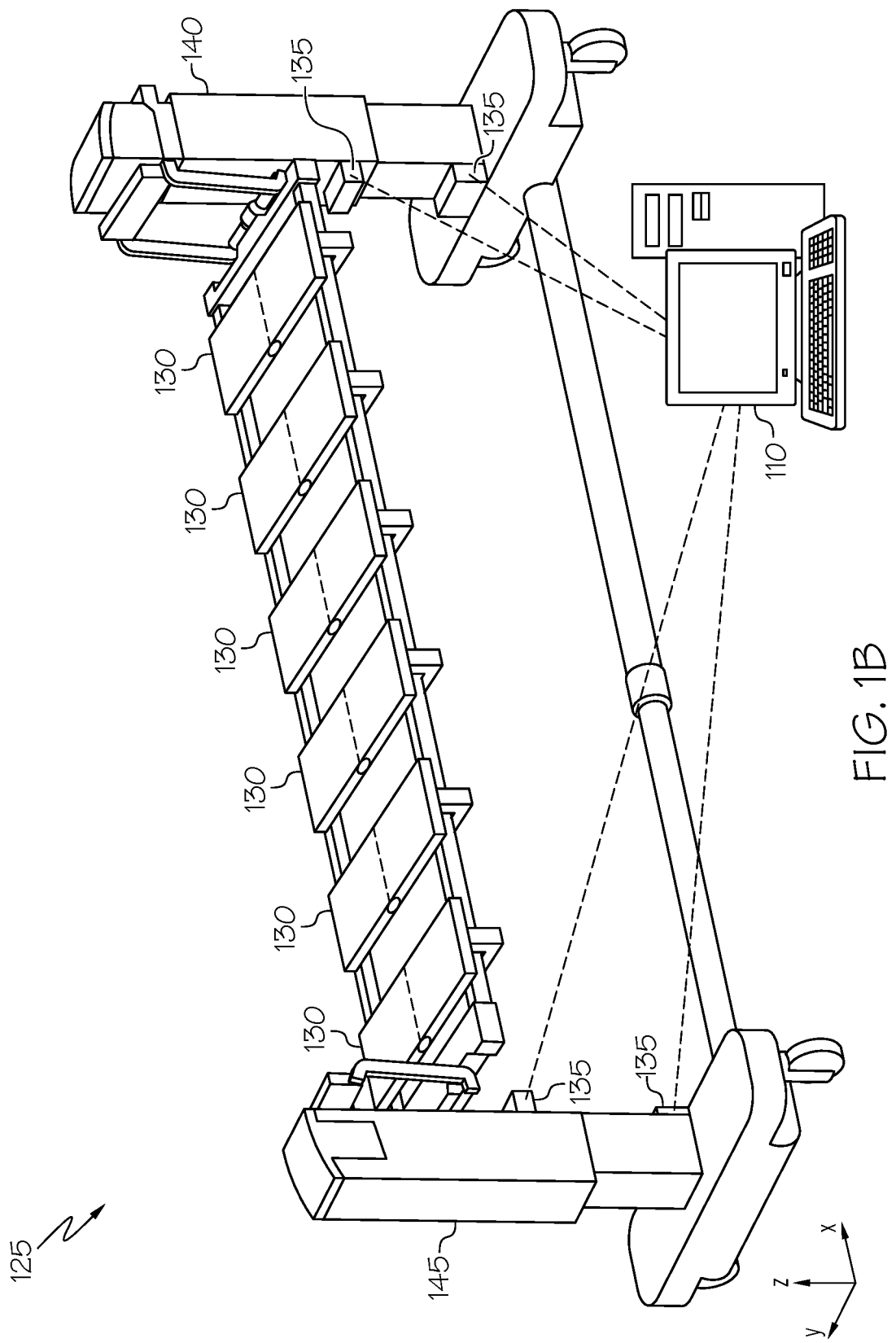
FIG. 1B schematically depicts an illustrative surface of a subject tracking system according to one or more embodiments shown or described herein.

The surface 125 is generally any supportive component for supporting the subject 115, particularly when the subject 115 is receiving medical care, such as, for example, undergoing a surgical procedure. In some nonlimiting examples, the surface 125 may be an operating table, a gurney, a hospital bed, and/or a person support apparatus. In some embodiments, the surface 125 may be a person support apparatus that supports the subject 115 during a spinal surgical procedure in which the subject 115 may be positioned or moved during the procedure. FIG. 1B depicts one such illustrative surface 125. As depicted in FIG. 1B, the surface 125 may be an automated or semi-automated person support apparatus that is used for a spinal procedure, which includes one or more movable support components 130 and one or more control devices 135.

The one or more movable support components 130 may be components that support a subject thereon and are movable to position and/or reposition the subject. At least a portion of the one or more movable support components 130 may move in any direction to position or break a subject supported thereon, such as to establish a baseline positioning for a first spinal procedure or a first portion of a spinal procedure, and subsequently move to position or break the subject in a second position for a second spinal procedure or a second portion of a spinal procedure. For example, at least a portion of the one or movable support components 130 may move up or down in a vertical direction (e.g., along the z-axis), or sideways in a horizontal direction (e.g., in the x-y plane). In some embodiments, at least a portion of the one or more movable support components 130 may move relative to one or more other portions of the surface 125. In some embodiments, a first portion of a movable support component 130 may move relative to a second portion of the movable support component 130 such that the first portion and the second portion fold the movable support component 130 along an axis (represented by the dashed line).

In some embodiments, the surface 125 may further be adjustable by incorporating one or more additional movable components for moving or positioning the subject 115 (FIG. 1) supported thereon. For example, the surface 125 may include a first movable column 140 and a second movable column 145, each of which extends and retracts in the vertical direction independently or in conjunction with one another to move the subject 115 (FIG. 1) up or down in the vertical direction. For example, the first column 140 may be extended relative to the second column 145 to achieve an inclined surface 125 so as to place the subject 115 (FIG. 1) in a Trendelenburg or reverse Trendelenburg position.

The one or more control devices 135 may control movement of the one or more movable support components 130, the first movable column 140, and/or the second movable column 145. That is, the one or more control devices 135 may incorporate or be communicatively coupled to one or more movement mechanisms (not shown), such as, for example, an actuator, a rotation mechanism, an inflatable bladder, and/or the like that causes the one or more movable support components 130, the first movable column 140, and/or the second movable column 145 to move.

In various embodiments, the one or more control devices 135 may be communicatively coupled to the computing device 110. As such, the computing device 110 may transmit one or more signals to the one or more control devices 135. In response to the one or more signals received from the computing device 110, the one or more control devices 135 may cause the one or more movable support components 130, the first movable column 140, and/or the second movable column 145 to move, thereby moving or positioning a subject thereon. In some embodiments, the one or more control devices 135 may be directed to move independently of signals received from the computing device 110. For example, the one or more control devices 135 may incorporate a user interface (e.g., a foot pedal or the like) that allows a user to direct the one or more control devices 135 to move the one or more movable support components 130.

It should be understood that the surface 125 depicted in FIG. 1B is merely illustrative, and other surfaces that move or position a subject thereon are contemplated and possible. In addition, the surface 125 may be manually controlled to move or position a subject thereon.

Figure 4:
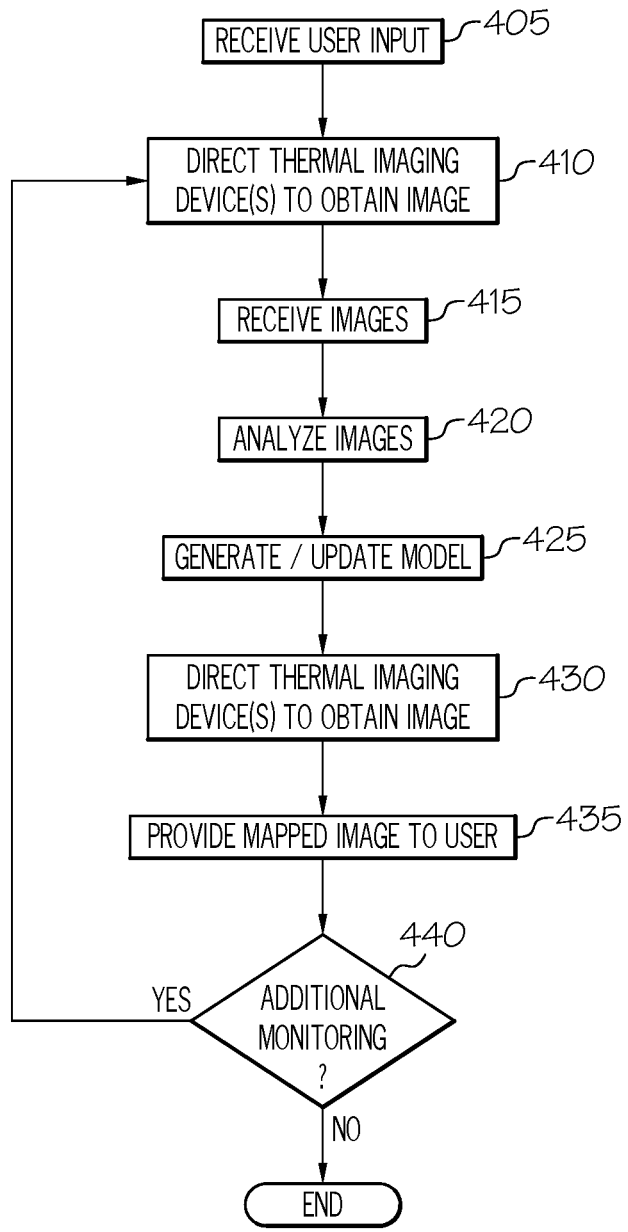
FIG. 4 schematically depicts a flow diagram of an illustrative method of obtaining an image and determining a subject positioning according to one or more embodiments shown or described herein.

The various processes that may be carried out by the computing device 110 in obtaining image data from each thermal imaging device 105, generating a model, and providing a user interface is depicted in flow diagram of FIG. 4. Each of the processes described with respect to FIG. 4 may be embodied by one or more programmed instructions stored on one or more memory devices, such as the RAM 310 or the ROM 315 (FIG. 3) described herein.

Prior to beginning the processes described with respect to FIG. 4, the one or more thermal markers 120 may be placed on the subject 115, the surface 125 supporting the subject 115, and/or on one or more other objects. That is, prior to capturing thermal images of the subject 115, the surface 125, and/or the other objects, the one or more thermal markers 120 may be placed in a desired location. For example, if a subject's spine is to be imaged, each of the one or more thermal markers 120 may be placed on each vertebra of the subject, or at another suitable location. The one or more thermal markers 120 may generally be placed by surgical personnel, and may optionally be placed according to one or more instructions provided by the computing device 110. Alternatively, the one or more thermal markers 120 may be placed and a user may input the approximate location of the thermal markers 120 into the computing device 110 (e.g., "head", "elbow", "knee", etc.).

Referring to FIGS. 1A and 4, in step 405, the computing device 110 may receive a user input to begin tracking subject positioning. It should be understood that step 405 is optional. That is, in some embodiments, the computing device 110 may not receive a user input to begin tracking subject positioning. For example, the computing device 110 may recognize when a subject 115 is within the field of view of each thermal imaging device 105 and begin tracking, or the computing device 110 may be in an "always on" state when powered on such that it is ready to complete the various processes described with respect to FIG. 4 without any user input.

In some embodiments, the computing device 110 may direct each thermal imaging device 105 to obtain the thermal images in step 410. For example, the computing device 110 may direct each thermal imaging device 105 by transmitting a signal to each thermal imaging device 105. It should be understood that step 410 is optional. That is, in some embodiments, each thermal imaging device 105 may obtain thermal images and/or transmit data without direction from the computing device 110. For example, each thermal imaging device 105 may automatically obtain thermal images and/or transmit data when powered on.

In step 415, the computing device 110 receives the thermal images from each thermal imaging device 105. The thermal images may be in the form of image data. Thus, the thermal images may be transmitted as image data from each thermal imaging device 105 to the computing device 110. The computing device 110 analyzes the thermal images in step 420. The thermal images are generally analyzed to determine a shape and positioning of the subject 115, which may be based on the location and positioning of the subject 115, location and positioning of certain body parts of the subject 115, the surface 125, other objects, and/or the thermal markers 120. The thermal images may also be analyzed to determine a location of the thermal markers 120. Based on this initially-obtained and analyzed image data from the thermal imaging devices 105 according to steps 415 and 420, the computing device 110 may use the location and positioning of the subject's body, parts thereof, and the thermal markers 120 as a baseline image for establishing whether the subject 115 is moved from that initial positioning thereafter, as a guideline for returning the subject 115 back to the initial positioning, and/or for a determination as to whether the subject 115 is appropriately positioned.

Figure 5:
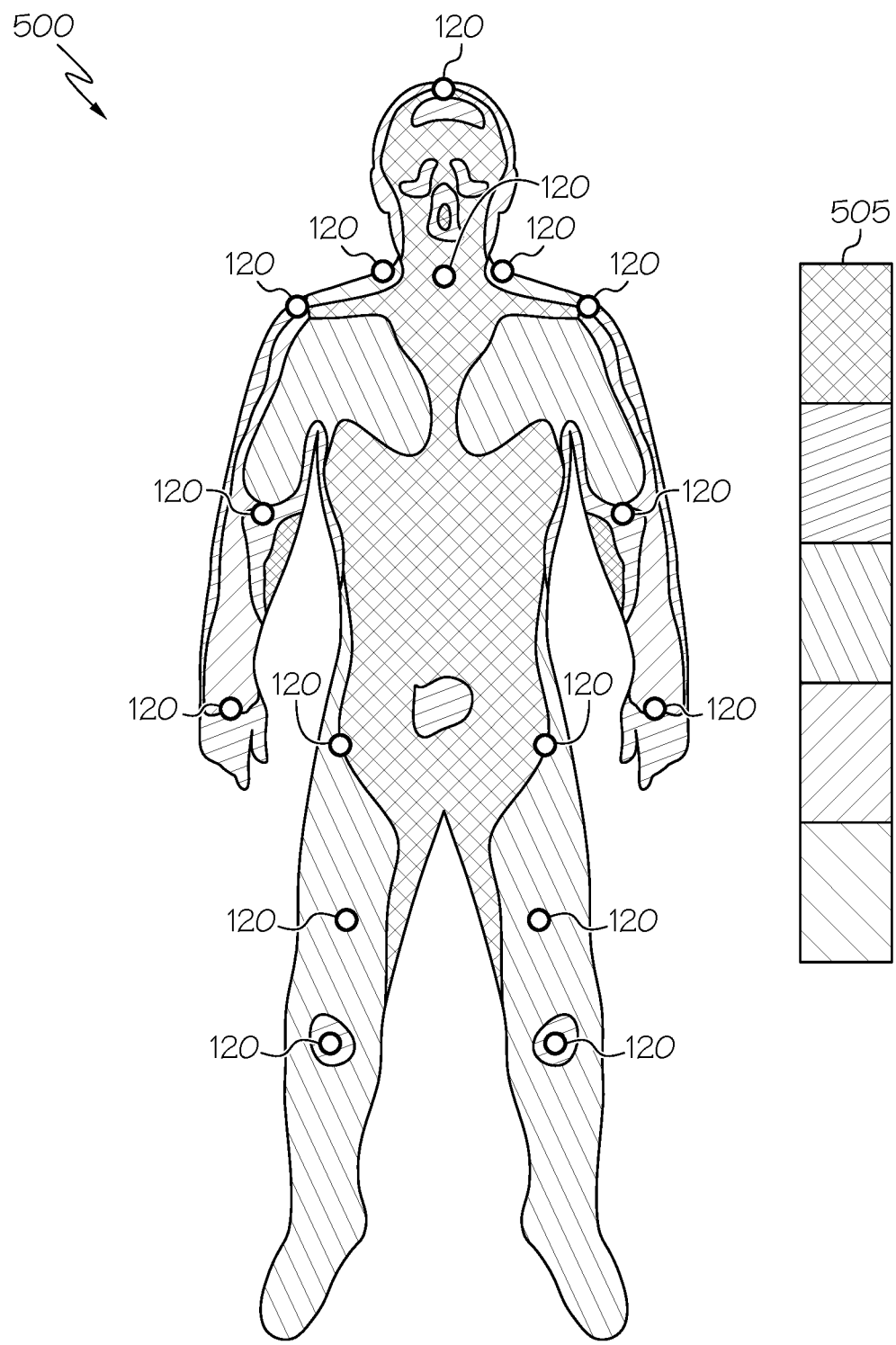
FIG. 5 schematically depicts illustrative thermal markers on a subject as imaged by a thermal imaging device according to one or more embodiments shown or described herein.

Referring now to FIGS. 1A and 5, FIG. 5 is a pictorial representation of illustrative image data obtained by a thermal imaging device 105 and transmitted to the computing device 110. As shown in FIG. 5, a thermal image 500 of the subject 115 indicates the relative temperature of thermal energy radiated by various portions of the subject's body. In some embodiments, the thermal image 500 may include a scale 505 that indicates the relative temperature of the thermal energy radiated by different portions of the subject's body based on the temperature of IR radiation that is detected by the thermal imaging device 105. For example, in some embodiments, the scale 505 may range from the coolest portions of the subject's body (lowest temperature of IR radiation detected) at the bottom and the highest portions of the subject's body (highest temperature of IR radiation detected) at the top.

Since the subject 115 may generally radiate more thermal energy than surrounding objects, the computing device 110 may determine an outline of the subject's body and/or various body features based on the thermal energy radiating therefrom when completing step 420 (FIG. 4) by, for example, thresholding the image to isolate the subject 115 from cooler portions of the collected image. For example, the computing device 110 may determine the outline of the subject 115 based on a change in the temperature of the thermal energy (e.g., the subject's body will generally radiate thermal energy within a first particular range and the area immediately surrounding the subject's body radiates thermal energy within a second particular range different than the first). In addition, the computing device 110 may determine certain features of the subject 115 based on the thermal energy radiated therefrom. For example, the extremities of the subject (e.g., the limbs, feet, hands, etc.) may radiate thermal energy at a lower temperature than, for example, the torso or the head. The computing device 110 may recognize a subject's torso because it radiates more thermal energy than the subject's extremities (e.g., fingers, toes, and/or the like) in conjunction with the general shape and relative positioning of the torso.

In addition, the thermal markers 120 may be positioned at particular locations on the subject 115 to serve as reference points that are used by the computing device 110 in determining the positioning of the subject and the various locations of certain portions of the subject. In some embodiments, the computing device 110 may recognize the positioning of the subject 115 based upon a particular placement of the thermal imaging devices 105 with respect to the subject's body and/or parts thereof. For example, prior to imaging, the computing device 110 may direct a user to place thermal markers 120 at specified locations on the subject or the computing device 110 may receive inputs from a user that indicate where thermal markers 120 have been placed. In other embodiments, the computing device 110 may automatically determine positioning of the subject 115 based on a recognition of the location, size, shape, and/or temperature of the thermal energy radiated by the subject 115 and/or the thermal markers 120 without any user inputs. In some embodiments, the computing device 110 may determine particular parts of the subject's body based on the type of thermal marker 120 placed thereon. For example, one or more first thermal markers that radiate thermal energy at a first temperature may be placed on the subject's torso and recognized by the computing device 110 as such. In addition, one or more second thermal markers that radiate thermal energy at a second temperature may be placed on the subject's arms and legs and recognized by the computing device 110 as such. In some embodiments, an initial determination of the positioning of the subject 115 may be used as a baseline for additional analysis, such as analysis after the subject 115 is moved or repositioned.

Referring again to FIGS. 1A and 4, the computing device 110 generates a model from the analyzed images in step 425.

Figure 6C:
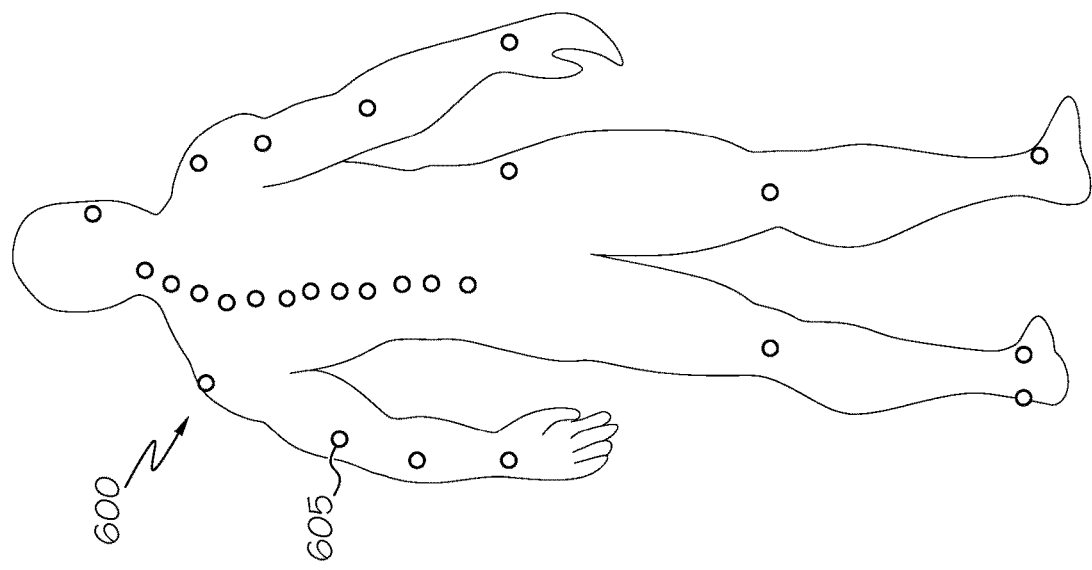
FIG. 6C schematically depicts a perspective rear view of an illustrative three dimensional model of a subject according to one or more embodiments shown or described herein.
Figure 6B:
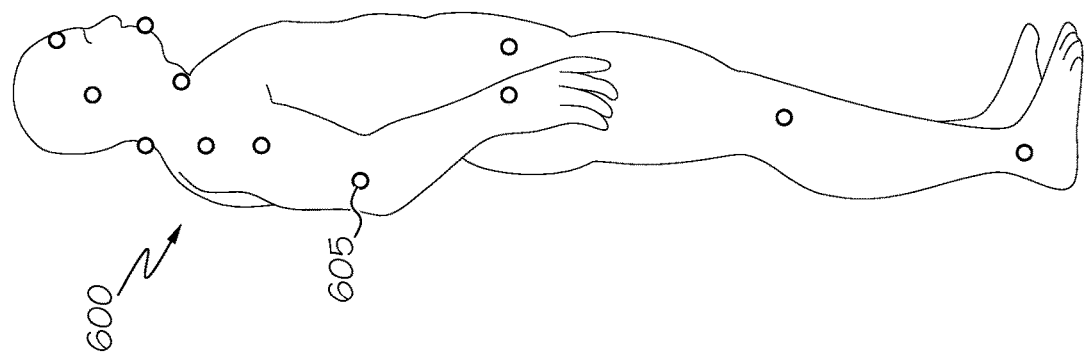
FIG. 6B schematically depicts a side view of an illustrative three dimensional model of a subject according to one or more embodiments shown or described herein.
Figure 6A:
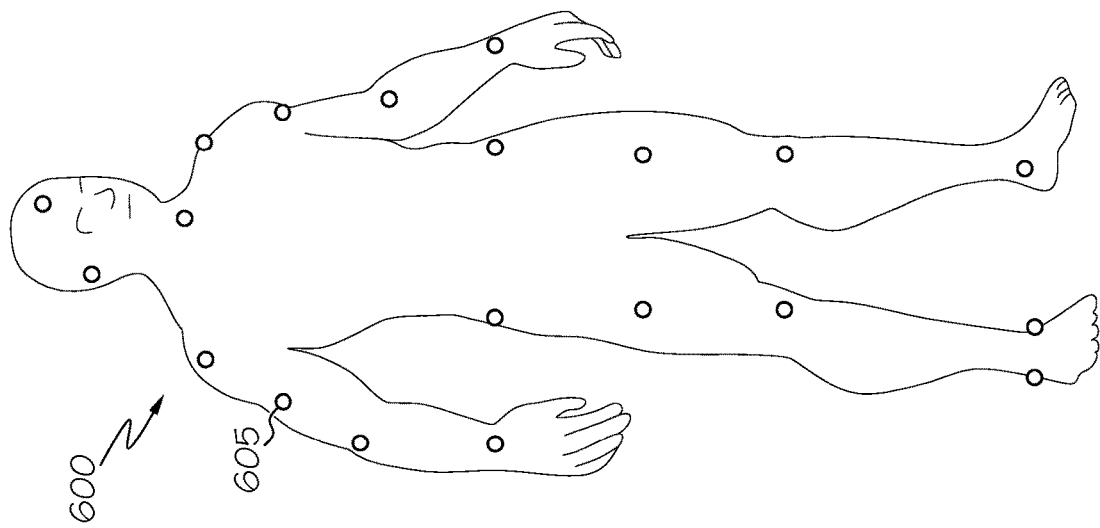
FIG. 6A schematically depicts a perspective front view of an illustrative three dimensional model of a subject according to one or more embodiments shown or described herein.

A model may be generated as a scaled representation of the subject 115, including various body features of the subject 115, which is based on information contained in the thermal images. As part of generating the model, the computing device 110 may further map the locations of the thermal markers 120 as indicators on the model in step 430. FIGS. 6A-6C depict an illustrative model that may be generated by the computing device 110 with indicators mapped thereon. Referring also to FIG. 1A, the model 600 may generally be a computer-generated representation of the subject's body that is based on the information contained in the image data received from each thermal imaging device 105. In some embodiments, the model 600 may be a two dimensional representation of the image data. In other embodiments, the model 600 may be a three dimensional representation of the image data, particularly in embodiments where image data is obtained from a plurality of thermal imaging devices 105 spaced apart from each other such that the respective optical axis 106 of each thermal imaging device 105 is at a different angle relative to the surface 125 supporting the subject 115.

In various embodiments, the model 600 may be constructed by the computing device 110 such that the shapes and various dimensions thereof reflect the shapes and various dimensions of the subject that is imaged by the one or more thermal imaging devices 105. In some embodiments, the model 600 may include a plurality of indicators 605 thereon that correspond to the thermal markers 120. That is, each of the indicators 605 on the model 600 corresponds to a thermal marker 120 on the subject 115. Thus, if a thermal marker 120 is placed on the right elbow of the subject 115, the computing device 110 recognizes the location from the image data and places a corresponding indicator 605 on the right elbow of the model 600. Accordingly, when the model 600 is displayed by the computing device 110, it appears to a user as a representation of the subject 115 with the thermal markers 120 thereon. In other embodiments, the model 600 may be generated without the indicators 605 thereon. That is, the model 600 may represent the positioning of the subject 115 based on the location and positioning of the thermal markers 120, but such a location and positioning of the thermal markers 120 are not displayed as the indicators 605.

Figure 7:
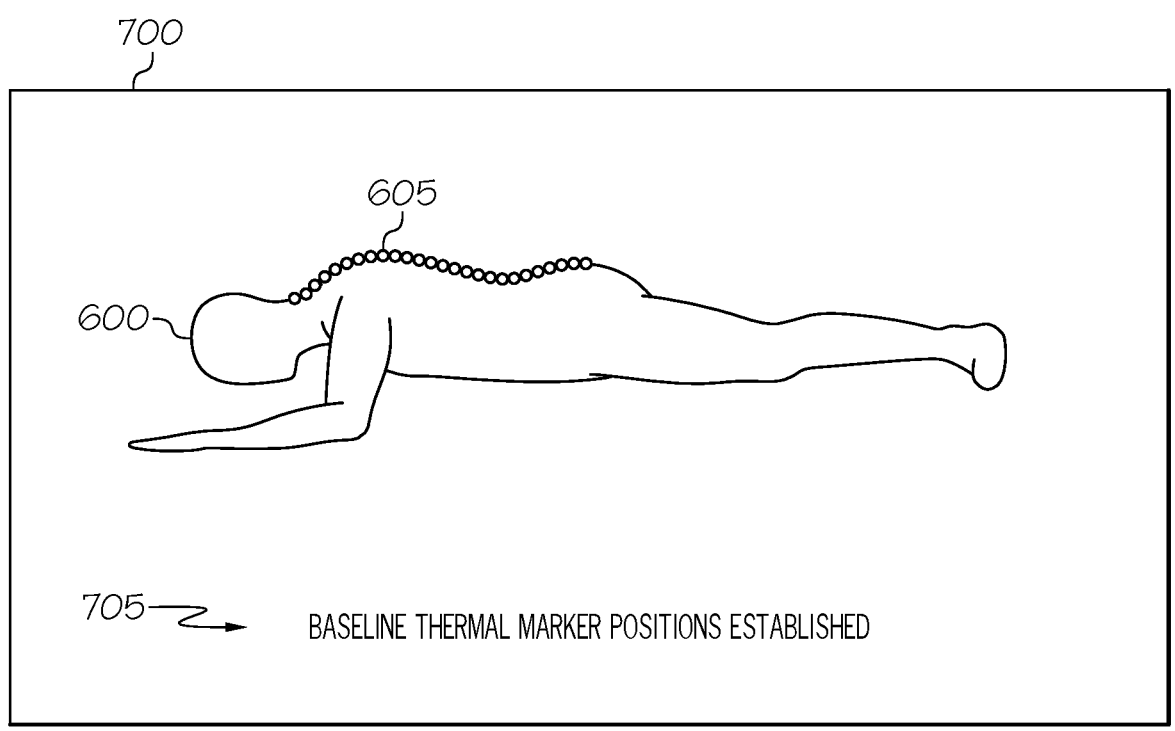
FIG. 7 schematically depicts an illustrative screen shot of a user interface according to one or more embodiments shown or described herein.

Referring again to FIGS. 1A and 4, in step 435, the computing device 110 may provide the mapped model to a user via a user interface. For example, the computing device 110 may have a user interface that displays the model 600, as shown in FIG. 7. Referring to FIGS. 1A and 7, the user interface 700 may provide the model 600 displayed with the mapped indicators 605 thereon. In addition, the user interface 700 may provide additional information 705 that is displayed to the user. In a nonlimiting example, the additional information 705 may be a status message such as "BASELINE THERMAL MARKER POSITIONS ESTABLISHED," which may indicate that the computing device 110 has obtained and processed the thermal images from each thermal imaging device 105 when the subject 115 is in an initial positioning (e.g., baseline position). In another nonlimiting example, the additional information 705 may be a message that the subject 115 is appropriately or inappropriately positioned based on a desired initial positioning/arrangement for a particular procedure. In some embodiments, the initial positioning may be, for example, the positioning of the subject 115 when the computing device 110 receives the first thermal images from the thermal imaging devices 105. In other embodiments, the initial positioning may be when the computing device 110 receives an input from a user indicating that the subject 115 is positioned in an initial/baseline positioning. In some embodiments, the initial positioning may be a position in which the subject 115 is prepared for a first surgical procedure or a first portion of a surgical procedure. In some embodiments, the initial positioning may be a position that is based on stored clinical data.

Referring again to FIGS. 1A and 4, the computing device 110 determines whether additional monitoring of the subject 115 is necessary in step 440. Such a determination may generally be based on one or more inputs received from a user and/or may be based on the type of monitoring for which the system 100 is configured. For example, in some embodiments, a user may only want to establish an initial baseline positioning of a subject and not conduct additional monitoring, such as in embodiments where the system 100 is used for periodic monitoring of a bedridden subject that is in traction. In such instances, the computing device 110 may receive an input that indicates that additional monitoring is not necessary or the computing device 110 may automatically be programmed to not conduct additional monitoring. Additional monitoring may be necessary to track movement and/or positioning of the subject 115 to determine whether the subject 115 has moved from the initial positioning, such as, for example, during a surgical procedure when the subject may begin at the baseline positioning for a first procedure or a first portion of the procedure, moved to a second positioning for a second procedure or a second portion of the procedure, and thereafter either returned to the baseline positioning or moved to a third positioning for a third procedure or third portion of the procedure. In such instances, the computing device may receive an input that indicates that additional monitoring should be completed, such as, for example, an input from a user indicating that the subject 115 is arranged in a baseline positioning or an input from a user requesting continuous monitoring.

If additional monitoring is necessary (e.g., to continuously monitor the subject 115), the process returns to step 410 to direct the thermal imaging device(s) 105 to obtain additional images. In embodiments where step 410 is omitted, the process may return to step 415 to receive additional images from each thermal imaging device 105. If no additional monitoring is necessary, the process may end.

Figure 9A:
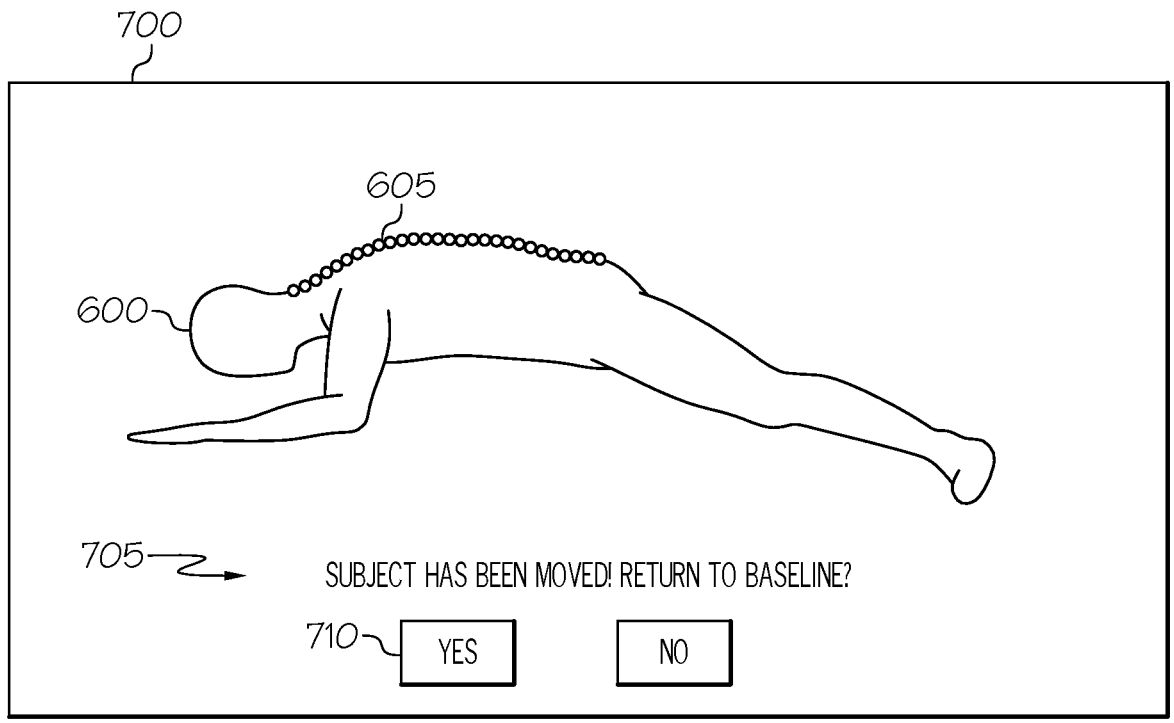
FIG. 9A schematically depicts another illustrative screen shot of a user interface according to one or more embodiments shown or described herein.

When additional monitoring is necessary and the process repeats, the model 600 may be continuously updated to reflect the subject positioning, such as when the subject is moved or repositioned. Accordingly, as shown in FIGS. 1A and 9A, the user interface 700 may provide the updated model 600 with the updated location of the indicators 605 thereon. For example, each thermal imaging device 105 may continuously image the subject 115 and the computing device 110 may continuously receive and analyze the image data (steps 415 and 420 in FIG. 4), which is used to continuously update the model 600 and the indicators 605 thereon to correspond to the current positioning of the subject 115 in the image data (steps 425 and 430 in FIG. 4). In some embodiments, continuously monitoring the subject 115 may include continuously receiving video images from the thermal imaging devices 105 and continuously analyzing the video images. In other embodiments, continuously monitoring the subject 115 may include periodically receiving images from the thermal imaging devices 105 and analyzing the images as they are received.

When the computing device 110 analyzes the images (step 420 in FIG. 4) and updates the model and thermal marker mapping (steps 425 and 430 in FIG. 4), the computing device 110 may further determine whether the subject 115 has moved. For example, the computing device 110 may recognize that the subject 115 is no longer in the initial baseline positioning that was established. That is, the computing device 110 may compare newly received images to the originally received baseline images and determine, through image analysis and based upon the comparison, whether the subject's body, portions thereof, and/or the thermal markers 120 are in the same location. The comparison may further account for any movement of the thermal imaging devices 105, adjustments of a field of view of the thermal imaging devices 105, and/or the like. For example, if a thermal imaging device 105 moves or changes the field of view, it may transmit coordinates and/or additional data to the computing device 110 indicating such a change so that the computing device 110 recognizes that change when analyzing the thermal images. If the subject's body, portions thereof, and/or the thermal markers 120 are in the same location, the computing device 110 may determine that the subject has not moved.

Figure 8:
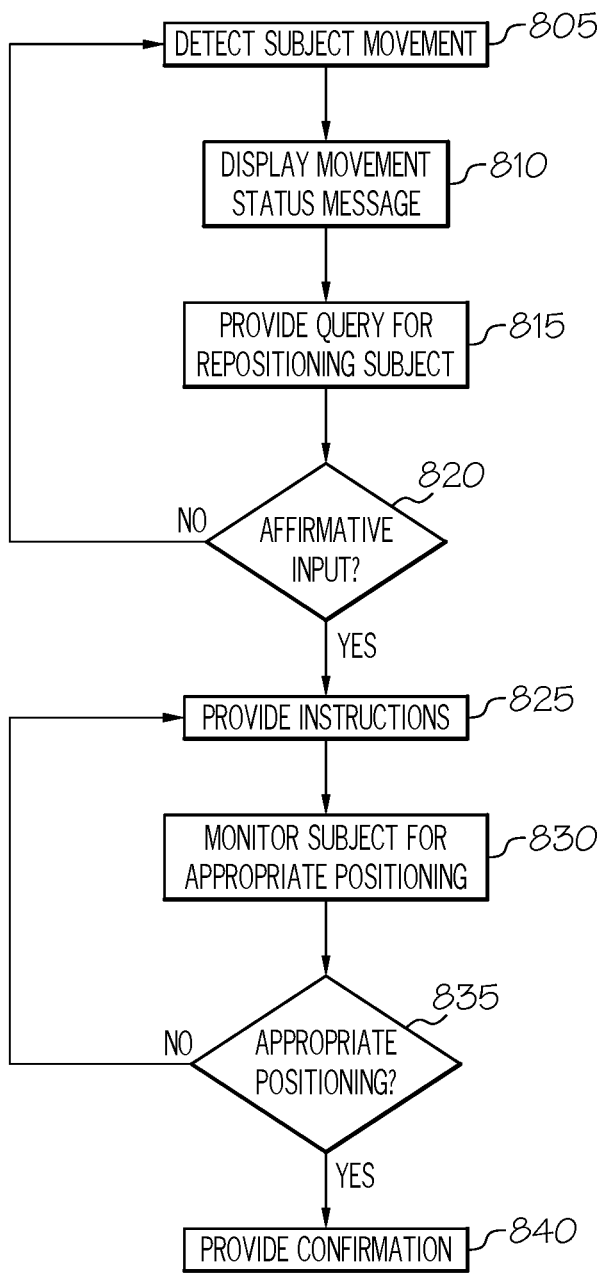
FIG. 8 schematically depicts a flow diagram of an illustrative method of providing a user interface and responding to user inputs according to one or more embodiments shown or described herein.

In some embodiments, as shown in FIG. 8, the computing device 110 may detect subject movement in step 805, such as when the computing device 110, upon completing the comparison, recognizes that the subject's body, portions thereof, and/or the thermal markers 120 are no longer in the same location as the subject's body, portions thereof and/or the thermal markers 120 in the baseline images. When the comparison indicates subject movement, the computing device 110 may provide additional information, via the user interface, to notify a user of the detected movement. For example, the computing device 110 displays a movement status message in step 810. In a nonlimiting example, the additional information 705 provided by the user interface 700 may be a status message such as "SUBJECT HAS BEEN MOVED! RETURN TO BASELINE?" as depicted in FIG. 9A.

In some embodiments, a user may choose to return the subject to the baseline positioning, such as, for example, in embodiments where a first portion of a surgical procedure is completed at the baseline positioning, the subject is repositioned for a second portion of the surgical procedure, and then returned to the baseline positioning for a third portion of the surgical procedure. Referring again to FIGS. 1A and 8, the computing device 110 provides a query for repositioning the subject 115 in step 815. For example, the computing device 110 may provide a user input option 710 that includes "YES" and "NO" buttons, as depicted in FIG. 9A. The buttons may be actuated by the user to either receive instructions or not receive instructions.

If the user selects "NO" in the user interface, the computing device 110 determines in step 820 that an affirmative input was not received, and may return to step 805 to continue receiving images from the thermal imaging devices 105 and comparing the received images to baseline images and/or updated images that indicate subject movement to determine whether the subject 115 is moved additional times to an additional positioning.

If the user selects "YES" in the user interface, the computing device 110 determines in step 820 that an affirmative input has been received by the user, and subsequently provides instructions for moving the subject 115 in step 825 or alternatively automatically directs the surface 125 to move. In embodiments, the computing device 110 may provide instructions by determining how the updated images differ from the baseline image, determining particular movements that would result in a return to a positioning that corresponds to the baseline positioning, and generating instructions that direct a user to complete the particular movements on the subject. Determining how the updated images differ for the purposes of providing instructions may include determining where each reference point on the subject's body, a part thereof, and/or the thermal markers 120 has moved relative to its baseline positioning. As noted above, the movement relative to the baseline positioning may be determined through a comparison of the baseline image and the updated image with the use of image analysis to detect features of the subject and/or the thermal markers. Determining particular movements may include calculating certain body movements that would result in a return to the baseline positioning, which may be based on, for example, body mechanics data and/or the like. In some embodiments, determining particular movements may include determining a particular positioning or arrangement of the surface 125 that would result in a return to the baseline positioning, which may be based on, for example, surface movement data and/or the like.

For example, using image analysis of the baseline image and the updated image, the computing device 110 determines the difference in the location of the same thermal markers on the baseline image and the updated image. Based on the difference in location of the thermal markers 120 between the baseline image and the updated image and the general positioning of the thermal markers on the subject 115, the computing device 110 may determine one or more corrective movements to apply to the subject 115 which would result in repositioning the thermal markers 120 in the updated image to their initial location in the baseline image. For example, if a subject has been repositioned to impart a curvature to the spine, as indicated in FIG. 9A and as determined by the location of the thermal markers in the baseline image and the thermal markers in the updated image, the computing device 110 determines a corrective movement which would align the thermal markers in the updated image with the thermal markers in the baseline image. In some embodiments, the computing device 110 may provide a user with a visual and/or audible signal indicating directions of movement that would restore the subject to the positioning in the baseline image.

In other embodiments, such as when the surface 125 is an automated or semi-automated surface (such as the automated or semi-automated person support apparatus depicted in FIG. 1B), the computing device 110 may provide instructions to the surface 125 such that the surface 125 (or portions thereof) is actuated to return the subject 115 to the position indicated in the baseline image. For example, referring also to FIG. 1B, the computing device 110 may transmit one or more signals to the one or more control devices 135 while continuously monitoring the position of the subject with the captured thermal images. The one or more control devices 135 direct movement of the one or more movable support components 130, the first movable column 140, and/or the second movable column 145 to cause the subject 115 to move. In some embodiments, the computing device 110 may also transmit a stop signal or the like to the one or more control devices 135, which, in turn, direct the one or more movable support components 130, the first movable column 140, and/or the second movable column 145 to stop moving once the subject has been returned to the position indicated in the baseline image.

Figure 9B:
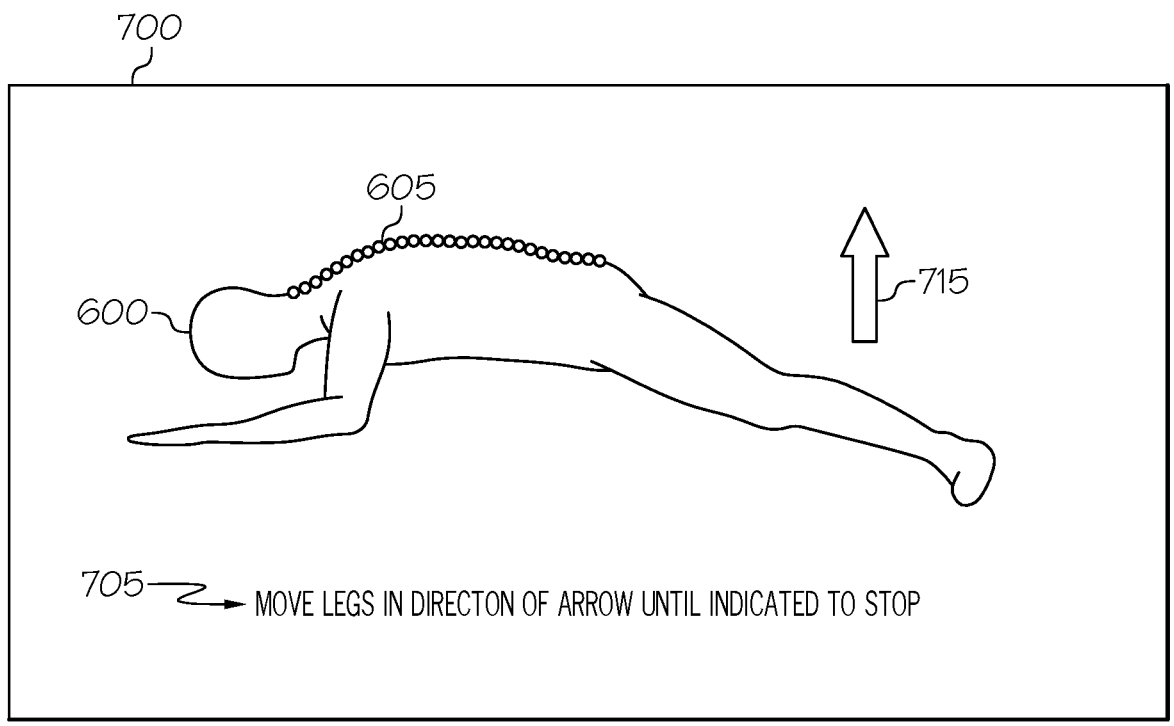
FIG. 9B schematically depicts another illustrative screen shot of a user interface according to one or more embodiments shown or described herein.

In some embodiments, the computing device 110 may automatically transmit signals to the one or more control devices 135 to move the one or more movable support components 130 without further user input. In other embodiments, the computing device may provide a user with instructions for moving the subject. In turn, the user may manually adjust the surface 125 or may provide one or more user inputs that direct the one or more control devices 135 to move. FIG. 9B depicts one embodiment of a visual instruction provided to a user by the computing device 110 to assist in returning the subject to the position captured in the baseline image. In this embodiment, the computing device 110, via the user interface 700, provides additional information 705 that states "MOVE LEGS IN DIRECTION OF ARROW UNTIL INDICATED TO STOP". In this embodiment, the computing device 110 will monitor the position of the thermal markers 120 with the thermal imaging devices 105 in substantially real time and capture a sequence of updated images as the subject is repositioned based on the instructions provided on the user interface 700. When the thermal markers from the updated images are co-located with the corresponding thermal markers in the baseline image, the computing device provides the user with a "STOP" audible and/or visual indication via the user interface 700.

For example, in some embodiments, one or more directional arrows 715 or the like at particular locations with respect to the subject 115 may be provided via the user interface, where the directional arrows 715 provide a visual indicator of how the subject 115 is to be moved to effect a desired positioning. If more than one directional arrow 715 is provided, the directional arrows 715 may be provided simultaneously or may be provided consecutively, such as, for example, for each consecutive movement that is to be completed to adjust the subject 115 to a desired positioning. In another example, the computing device 110 may provide instructions by transmitting one or more signals to the surface 125, where the one or more signals direct the surface 125 to move to a particular positioning that corresponds to a desired positioning of the subject 115.

Referring again to FIGS. 1A and 8, the computing device 110 monitors the subject 115 for an appropriate positioning in step 830. That is, the computing device 110 continuously receives images from each thermal imaging device 105, analyzes the images, updates the model, and maps the thermal marker locations (steps 415-430 of FIG. 4), and compares the updated model with previously received thermal images and/or the previously updated model to determine whether the subject 115 has been moved to a new positioning. For example, the computing device 110 may recognize that the subject has been moved to the new positioning when the positioning of the subject's body, parts thereof, and/or the thermal markers 120 in the thermal images that were most recently received do not correspond to the positioning in the thermal images when the subject was initially determined to have been moved. In some embodiments, the new positioning may correspond to the baseline positioning. In other embodiments, the new positioning may correspond to another positioning.

If the subject 115 has been moved to a new positioning, the computing device 110 determines in step 835 whether the new positioning is an appropriate positioning. An appropriate positioning may generally be a desired positioning such as, for example, the initial positioning (baseline positioning), a positioning necessary to complete a particular surgical procedure, and/or the like. Such a positioning necessary to complete a particular surgical procedure may be based upon inputs received from a user, body positioning data, body mechanics data, positioning data for the surface 125, and/or the like. For example, before a surgical procedure is completed, the subject 115 may be moved to each desired positioning and recorded. That is, the subject 115 may be moved, for example, to the baseline positioning and the computing device 110 may receive an input indicating the baseline. Subsequently, the subject 115 may be moved to one or more other desired positions and at each position, the computing device 110 may receive an input indicating such a position. Each time the computing device 110 receives an input indicating a desired positioning, it may record the image data and/or the model generated therefrom.

The computing device 110 determines whether the positioning is appropriate by determining, from the image data, whether the positioning of the subject corresponds to the stored image data of the appropriate positioning. For example, if the subject's body, parts thereof, and/or the thermal markers 120 obtained from the image data correspond in location and arrangement to stored image data of an appropriate positioning, the computing device 110 may determine that the subject is appropriately positioned. In some embodiments, the subject's body, parts thereof, and/or the thermal markers 120 obtained from the image data must be an exact match to the stored image data for an appropriate positioning determination. In other embodiments, the subject's body, parts thereof, and/or the thermal markers 120 obtained from the image data may be an approximate match to the store image data for an appropriate positioning determination. An approximate match may be, for example, a match within a determined range of positions that are acceptable.

If the computing device determines that the positioning is not appropriate (i.e., the subject's body, parts thereof, and/or the thermal markers 120 obtained from the image data do not correspond in location and arrangement to the stored image data), the computing device 110 returns to step 825 to provide additional instructions for moving the subject 115. If the positioning is appropriate, the computing device 110 provides a confirmation 840, such as, for example, a message in the additional information 705 (FIG. 9B) that states the positioning is correct, a message to stop movement of the subject, and/or the like.

In some embodiments, in lieu of directing a user to move the subject 115 between various positions, the computing device 110 may display a query asking the user if automatic repositioning is desired. If a user provides an affirmative input to the query, the computing device 110 may transmit one or more signals to the surface 125 that direct the surface to move and/or reposition the subject to a baseline positioning, an appropriate positioning, and/or the like. Alternatively, the computing device 110 may provide controls via the user interface, where the controls allow a user to electronically manipulate the surface 125, such as to move the subject to a baseline positioning, an appropriate positioning, and/or the like.

It should be understood that the user interface depicted and described with respect to FIGS. 7 and 9A-7B is merely illustrative, and that other user interfaces may be used without departing from the scope of the present disclosure.

A user that uses the system 100 to determine a positioning of the subject generally places the thermal markers 120 on the body of the subject 115 and further arranges the thermal imaging devices 105 to capture the thermal images of the subject. Placing the thermal markers 120 on the body of the subject 115 may be completed such that the markers 120 are particularly placed based upon instructions received from the computing device 110 or are particularly placed based on the user's determination of where the thermal markers 120 should be located. For example, if the subject 115 is to have spinal surgery, the user may place the thermal markers 120 at particular locations on the subject that would be appropriate for determining the positioning during the spinal procedure (e.g., on the posterior of the subject, such as over vertebra of the spine, on the posterior of the shoulders, etc.). In addition, the user may optionally arrange the thermal imaging devices 105 in such a manner so as to ensure each of the thermal imaging devices 105 captures a different angle of the subject 115, thereby allowing for a three dimensional model of the subject 115 to be generated by the computing device 110.

Optionally, after the thermal markers 120 have been placed on the subject 115, one or more desired positions that are necessary for completing the procedure may be established. For example, the user may move the subject 115 to a baseline positioning and provide an input to the computing device 110 that indicates the subject is in the baseline positioning, which allows the computing device 110 to record the thermal images of the subject 115 in the baseline positioning. In addition, the user may move the subject 115 to any other desired positioning, such as an appropriate positioning necessary to complete a particular procedure, and provide an input to the computing device 110 that indicates that the subject is in the other desired positioning, which allows the computing device 110 to record the thermal images of the subject 115 in the desired positioning. Such a process may be completed for each desired positioning.

In some embodiments where the user is completing a surgical procedure, the subject 115 may be placed in the baseline positioning to complete a first surgical procedure (or a first portion of the surgical procedure) and may subsequently be moved to the one or more other desired positions to complete one or more other surgical procedures (or one or more other portions of the surgical procedure). In some embodiments, the subject 115 may be returned to the baseline positioning to complete a final surgical procedure (or a final portion of the surgical procedure). Repositioning the subject 115 may be completed manually by the user, may be assisted by the computing device 110, which provides directions for moving the subject based on any recorded positioning information, or may be automatically completed by the computing device 110 and the surface 125. Accordingly, when the computing device 110 detects that the subject 115 has been moved, the user may decide whether to receive instructions from the computing device 110 for moving the subject 115 back to an original positioning or to a new positioning. If the user wishes to receive instructions, the user may move the subject based on the instructions until the computing device 110 indicates that the subject 115 has been appropriately positioned.

While embodiments of the subject tracking system have been described herein with reference to thermal markers attached to a subject, it should be understood that the same methods may be used with the thermal markers attached to the surface 125 and/or both the surface and the subject. For example, thermal markers may be attached to the surface 125 to determine a baseline positioning of the surface and, thereafter, to determine updated positioning of the surface 125 based on the captured thermal images. This information may be used to determine a difference in the positioning of the thermal markers, such as by image analysis, and, based on this difference, the computing device may determine movements of the surface to restore the position of the surface (and hence the subject) to the baseline positioning.

It should now be understood that the subject tracking system according to the present disclosure accurately tracks the position of a subject having a plurality of thermal markers thereon by imaging the subject and the thermal markers with one or more thermal imaging devices and processing the images with a computing device. As a result, the positioning of the subject can be monitored and any movement of the subject can be detected. In addition, the computing device may provide an interface that can guide a user in moving the subject to a new positioning or to return the subject back to an original positioning based on the thermal images received from the one or more thermal imaging devices.

While embodiments of the subject tracking system have been described herein with reference to a single surgical procedure, it should be understood that the subject tracking system may be used to assist with subject positioning during subsequent surgical procedures. For example, where a given surgical procedure requires a follow-up procedure, positioning data collected during the first surgical procedure may be utilized to replicate subject positioning during the second surgical procedure. In this application, the positioning data (baseline images, updated images, model, and the like) may be stored in a memory operatively associated with the subject tracking system and indexed according to identifying indicia associated with the subject.

Specific embodiments of the above-mentioned systems and methods may include, for example, a system for displaying a model of a subject. The system comprises one or more thermal imaging devices and a computing device communicatively coupled to the one or more thermal imaging devices, wherein the computing device comprises a processing device and a non-transitory, processor-readable storage medium comprising one or more processor readable and executable instructions that, when executed, cause the processing device to (1) receive one or more infrared images from the one or more thermal imaging devices, the one or more infrared images containing a plurality of thermal markers positioned relative to a surface, wherein at least one of the plurality of thermal markers is positioned on a subject located on the surface, (2) determine a location of the plurality of thermal markers with respect to the subject from the one or more infrared images, wherein the plurality of thermal markers produce thermal energy that is identifiable and distinguishable from thermal energy emitted by the surface and the subject, (3) map the location of the plurality of thermal markers to a model that represents the subject and the positioning of the subject, and (4) display the model with a plurality of indicators thereon, wherein each of the plurality of indicators corresponds to each of the plurality of thermal markers. In some embodiments, the one or more infrared images are a first one or more infrared images and the non-transitory, processor-readable storage medium further comprises processor readable and executable instructions that, when executed, cause the processing device to receive a second one or more infrared images from the one or more thermal imaging devices, the second one or more infrared images containing the plurality of thermal markers and map the updated location of the plurality of thermal markers to the model. In some embodiments, the non-transitory, processor-readable storage medium further comprises processor readable and executable instructions that, when executed, cause the processing device to determine whether the updated location of the plurality of thermal markers in the second one or more infrared images is different from the location of the plurality of thermal markers in the first one or more infrared images and when the updated location of the plurality of thermal markers in the second one or more infrared images is different from the location of the plurality of thermal markers in the first one or more infrared images, update the model to indicate a change in the positioning of the subject based on the difference in the location of the plurality of thermal markers and display an image of the updated model. In some embodiments, the non-transitory, processor-readable storage medium further comprises processor readable and executable instructions that, when executed, cause the processing device to display instructions for returning the subject to a positioning that corresponds to the location of the plurality of thermal markers from the first one or more infrared images. In some embodiments, the surface supporting the subject is communicatively coupled to the computing device, wherein the non-transitory, processor-readable storage medium further comprises processor readable and executable instructions that, when executed, cause the processing device to direct the surface to move from a first positioning to a second positioning based on the instructions. In some embodiments, the one or more thermal imaging devices comprise a plurality of thermal imaging devices, each of the plurality of thermal imaging devices having an optical axis, and individual thermal imaging devices of the plurality of thermal imaging devices are oriented such that each respective optical axis is at a different angle relative to the surface supporting the subject and the processor readable and executable instructions, when executed, further cause the processing device to receive one or more infrared images from each of the plurality of imaging devices. In some embodiments, the model is a three dimensional rendering of the subject that is generated from the one or more infrared images from each of the plurality of imaging devices.

Other specific embodiments of the above-mentioned systems and methods may include, for example, a method for tracking a positioning of a subject. The method comprises (1) receiving, by a processing device, one or more infrared images of the subject; (2) determining, by the processing device, a location of a plurality of thermal markers with respect to the subject from the one or more infrared images, wherein the plurality of thermal markers produce thermal energy that is distinguishable from thermal energy produced by the subject, and at least one thermal marker is located at a first location on a body of the subject; (3) mapping, by the processing device, the location of the plurality of thermal markers to a model that represents the subject and the positioning of the subject; and (4) displaying, by the processing device, the model with a plurality of indicators thereon, wherein the plurality of indicators corresponds to the plurality of thermal markers. In some embodiments, the one or more infrared images are a first one or more infrared images and the method further comprises: (1) receiving, by the processing device, a second one or more infrared images of the subject; (2) determining, by the processing device, an updated location of the plurality of thermal markers with respect to the subject from the second one or more infrared images; (3) mapping, by the processing device, the updated location of the plurality of thermal markers from the second one or more infrared images to the model; (4) determining, by the processing device, whether the updated location of the plurality of thermal markers in the second one or more infrared images is different from the location of the plurality of thermal markers in the first one or more infrared images; and when the updated location of the plurality of thermal markers in the second one or more infrared images is different from the location of the plurality of thermal markers in the first one or more infrared images, updating, by the processing device, the model to indicate a change in the positioning of the subject based on the difference in the location of the plurality of thermal markers and displaying, by the processing device, the updated model. In some embodiments, the method further comprises displaying, by the processing device, instructions for returning the subject to a positioning that corresponds to the location of the plurality of thermal markers from the first one or more infrared images. In some embodiments, the method further comprises directing, by the processing device, a surface supporting the subject to move from a first positioning to a second positioning. In some embodiments, the method further comprises receiving the one or more infrared images comprises receiving, by the processing device, one or more infrared images from a plurality of imaging devices and each of the plurality of thermal imaging devices comprises an optical axis, and individual thermal imaging devices of the plurality of thermal imaging devices are oriented such that each respective optical axis is at a different angle relative to a surface supporting the subject. In some embodiments, the method further comprises generating, by the processing device, the model as a three dimensional representation of the subject from the one or more infrared images from each of the plurality of imaging devices.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A system for positioning a subject on a surface, the system comprising:
    a plurality of thermal markers, each one of the plurality of thermal markers radiating thermal energy at a thermal marker temperature that differs from a subject temperature and a surface temperature, wherein a first thermal marker of the plurality of thermal markers is arranged at a first location relative to the surface;
    one or more thermal imaging devices arranged to capture a baseline infrared image and an updated infrared image of the surface and the plurality of thermal markers, wherein:
        the baseline infrared image comprises baseline image data that indicates an initial relative temperature corresponding to thermal energy radiated by the plurality of thermal markers relative to thermal energy radiated by the subject and the surface at a first point in time, and
        the updated infrared image comprises updated image data that indicates an updated relative temperature corresponding to thermal energy radiated by the plurality of thermal markers relative to thermal energy radiated by the subject and the surface at a second point in time subsequent to the first point in time; and
    a computing device communicatively coupled to the one or more thermal imaging devices, the computing device configured to:
        receive the baseline infrared image and the updated infrared image,
        distinguish the plurality of thermal markers from the subject and the surface by using the initial relative temperature from the baseline image data and the updated relative temperature from the updated image data to determine an outline of the subject and determine one or more areas corresponding to the plurality of thermal markers that are indicated in the baseline image data and the updated image data as being located adjacent to or within the outline of the subject and radiating a different temperature relative to the temperature radiated by the subject, and
        determine a corrective movement for at least one of the subject and the surface to align the plurality of thermal markers in the updated infrared image with the plurality of thermal markers in the baseline infrared image based on a location of the plurality of thermal markers in the baseline infrared image and a location of the plurality of thermal markers in the updated infrared image.

2. The system of claim 1, wherein at least one of the plurality of thermal markers is arranged on the surface.

3. The system of claim 1, wherein at least one of the plurality of thermal markers is arranged at or near a joint of the subject positioned on the surface.

4. The system of claim 1, wherein the plurality of thermal markers comprises one or more first thermal markers radiating thermal energy at a first thermal marker temperature and one or more second thermal markers radiating thermal energy at a second thermal marker temperature that is different from the first thermal marker temperature, wherein the first thermal marker temperature and the second thermal marker temperature are different from the subject temperature and the surface temperature.

5. The system of claim 1, wherein the one or more thermal imaging devices comprise a plurality of thermal imaging devices, each of the plurality of thermal imaging devices having an optical axis, and individual thermal imaging devices of the plurality of thermal imaging devices are oriented such that each respective optical axis is at a different angle relative to the surface.

6. The system of claim 5, wherein the computing device processes images from each of the plurality of thermal imaging devices and generates a three dimensional model based on the images.

7. The system of claim 1, wherein the computing device comprises a display that displays one or more models comprising a plurality of indicators that correspond to the plurality of thermal markers.

8. The system of claim 1, wherein the computing device provides and displays on a display device instructions for achieving the corrective movement based on the location of the plurality of thermal markers.

9. The system of claim 1, wherein the surface is communicatively coupled to the computing device, the computing device controlling positioning of the surface based on the corrective movement.

10. A method of positioning a subject on a surface, the method comprising:
    placing a plurality of thermal markers on a body of the subject, each one of the plurality of thermal markers radiating thermal energy at a thermal marker temperature that differs from a subject temperature and a surface temperature;
    capturing baseline infrared images of the subject and the plurality of thermal markers with one or more thermal imaging devices at a first point in time, the baseline infrared images comprising baseline image data that indicates an initial relative temperature corresponding to thermal energy radiated by the plurality of thermal markers relative to thermal energy radiated by the subject and the surface at the first point in time;
    capturing updated infrared images of the subject and the plurality of thermal markers with the one or more thermal imaging devices at a second point in time subsequent to the first point in time, the updated infrared image comprising updated image data that indicates an updated relative temperature corresponding to thermal energy radiated by the plurality of thermal markers relative to thermal energy radiated by the subject and the surface at the second point in time;

transmitting the baseline infrared images and the updated infrared images to a computing device, wherein the computing device distinguishes the plurality of thermal markers from the subject and the surface by using the initial relative temperature from the baseline image data and the updated relative temperature from the updated image data to determine an outline of the subject and determine one or more areas corresponding to the plurality of thermal markers that are indicated in the baseline image data and the updated image data as being located adjacent to or within the outline of the subject and radiating a different temperature relative to the temperature radiated by the subject and determines a corrective movement to align the plurality thermal markers in the updated infrared images with the plurality thermal markers in the baseline infrared images based on a location of the plurality of thermal markers in the baseline infrared images and a location of the plurality of thermal markers in the updated infrared images; and applying the corrective movement to at least one of the subject and the surface to position the subject on the surface.

11. The method of claim 10, wherein at least one of the plurality of thermal markers is arranged at or near a joint of the subject.

12. The method of claim 10, wherein the plurality of thermal markers comprises one or more first thermal markers radiating thermal energy at a first thermal marker temperature and one or more second thermal markers radiating thermal energy at a second thermal marker temperature that is different from the first thermal marker temperature, wherein the first thermal marker temperature and the second thermal marker temperature are different from the subject temperature and the surface temperature.

13. The method of claim 10, wherein the one or more thermal imaging devices comprise a plurality of thermal imaging devices, each of the plurality of thermal imaging devices having an optical axis, and individual thermal imaging devices of the plurality of thermal imaging devices are oriented such that each respective optical axis is at a different angle relative to the surface.

14. The method of claim 13, wherein the computing device processes images from each of the plurality of thermal imaging devices and generates a three dimensional model based on the images.

15. The method of claim 10, further comprising displaying, with the computing device, one or more models comprising a plurality of indicators that correspond to the plurality of thermal markers.

16. The method of claim 10, further comprising displaying, with the computing device, instructions for achieving the corrective movement based on the location of the plurality of thermal markers.

17. The method of claim 10, wherein:
the surface is communicatively coupled to the computing device; and
applying the corrective movement comprises the computing device sending control signals to the surface to position the surface according to the corrective movement.

18. A system for positioning a subject on a surface, the system comprising:
a plurality of thermal markers, wherein at least one of the plurality of thermal markers is arranged at or near a joint of the subject positioned on the surface and wherein each of the plurality of thermal markers radiates thermal energy at a temperature that is distinguishable from thermal energy emitted by the subject positioned on the surface, the surface, and one or more objects proximate the surface, wherein at least one of the plurality of thermal markers is arranged on the surface;
one or more thermal imaging devices arranged to capture a baseline infrared image and an updated infrared image of the surface and the plurality of thermal markers, wherein:
the baseline infrared image comprises baseline image data that indicates an initial relative temperature corresponding to thermal energy radiated by the plurality of thermal markers relative to thermal energy radiated by the subject and the surface at a first point in time, and
the updated infrared image comprises updated image data that indicates an updated relative temperature corresponding to thermal energy radiated by the plurality of thermal markers relative to thermal energy radiated by the subject and the surface at a second point in time subsequent to the first point in time; and
a computing device communicatively coupled to the one or more thermal imaging devices, the computing device configured to
receive the baseline infrared image and the updated infrared image,
distinguish the plurality of thermal markers from the subject and the surface by using the initial relative temperature from the baseline image data and the updated relative temperature from the updated image data to determine an outline of the subject and determine one or more areas corresponding to the plurality of thermal markers that are indicated in the baseline image data and the updated image data as being located adjacent to or within the outline of the subject and radiating a different temperature relative to the temperature radiated by the subject, and
determine a corrective movement for at least one of the subject and the surface to align the plurality of thermal markers in the updated infrared image with the plurality of thermal markers in the baseline infrared image based on a location of the plurality of thermal markers in the baseline infrared image and a location of the plurality of thermal markers in the updated infrared image.

19. The system of claim 18, wherein the plurality of thermal markers comprises one or more first thermal markers radiating thermal energy at a first temperature and one or more second thermal markers radiating thermal energy at a second temperature that is different from the first temperature.

20. The system of claim 18, wherein the surface is communicatively coupled to the computing device, the computing device controlling positioning of the surface based on the corrective movement.

* * * * *